(12) United States Patent
Umemoto et al.

(10) Patent No.: US 6,239,289 B1
(45) Date of Patent: May 29, 2001

(54) O-(PERFLUOROALKYL) DIBENZOFURANIUM SALT DERIVATIVES, INTERMEDIATES FOR THE PREPARATION OF THE SAME, PROCESS FOR THE PREPARATION OF THE INTERMEDIATES, PERFLUOROALKYLATING AGENTS, AND PROCESS FOR PERFLUOROALKYLATION

(75) Inventors: Teruo Umemoto, Westminster, CO (US); Kenji Adachi; Sumi Ishihara, both of Tsukuba (JP)

(73) Assignee: Daikin Industries Ltd., Osaka (JP)

( * ) Notice: Subject to any disclaimer, the term of this patent is extended or adjusted under 35 U.S.C. 154(b) by 0 days.

(21) Appl. No.: 09/463,706

(22) PCT Filed: Jul. 30, 1998

(86) PCT No.: PCT/JP98/03416

§ 371 Date: Feb. 15, 2000

§ 102(e) Date: Feb. 15, 2000

(87) PCT Pub. No.: WO99/06389

PCT Pub. Date: Feb. 11, 1999

(30) Foreign Application Priority Data

Aug. 1, 1997 (JP) .................................................... 9-207901

(51) Int. Cl.[7] ..................... C07C 211/45; C07C 245/08; C07C 245/20; C07D 307/91
(52) U.S. Cl. ......................... 549/212; 564/307; 534/562
(58) Field of Search ............................ 549/212; 564/452, 564/462, 307; 534/562

(56) References Cited

FOREIGN PATENT DOCUMENTS

7330703A * 12/1995 (JP).
9906389 * 2/1999 (WO).

* cited by examiner

Primary Examiner—Joseph K. McKane
Assistant Examiner—Taofiq A. Solola
(74) Attorney, Agent, or Firm—Armstrong, Westerman, Hattori, McLeland & Naughton, LLP

(57) ABSTRACT

O-(perfluoroalkyl)dibenzofuranium salt derivatives represented by the following general formula (1), General formula (1)

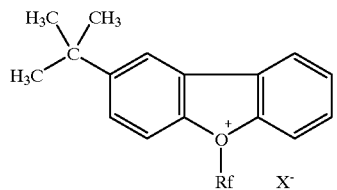

(wherein Rf in said general formula (1) is a C1–10 perfluoroalkyl group and X⁻ is a conjugate base of a Brönsted acid). Intermediates for preparation of the derivatives, a preparation method thereof, perfluoroalkylating agents comprising the said derivatives and the said preparation intermediates, and a perfluoroalkylating method.

10 Claims, No Drawings

O-(PERFLUOROALKYL) DIBENZOFURANIUM SALT DERIVATIVES, INTERMEDIATES FOR THE PREPARATION OF THE SAME, PROCESS FOR THE PREPARATION OF THE INTERMEDIATES, PERFLUOROALKYLATING AGENTS, AND PROCESS FOR PERFLUOROALKYLATION

This APPN. is a 371 of PCT/JP98/03416 filed Jul. 30, 1998.

FIELD OF THE INVENTION

The present invention relates to O-(perfluoroalkyl) dibenzofuranium salt derivatives which are useful as chemicals for introducing a perfluoroalkyl group into an oxygen atom, nitrogen atom and the like (hereinafter referred to as perfluoroalkylating agents), intermediates for their preparation, a preparation method for their intermediates, perfluoroalkylating agents and a perfluoroalkylation method.

PRIOR ART

For the conventional methods for perfluoroalkylating organic compounds, for example, the following synthetic methods for (trifluoromethyl)phenyl ether compounds by trifluoromethylation of phenolic compounds are known:

Method (1) of; preparing methylphenyl ether compounds by methylation of phenolic compounds, then leading to (trichloromethyl)phenyl ether compounds by selective chlorination of the side chains followed by conducting a halogen-exchange reaction with hydrogen fluoride in the presence of a catalyst (antimony pentachloride) [refer to Angew. Chem. Int. Ed. Engl., 16, 735 (1977)], Method (2) of: heating phenolic compounds with an excess of carbon tetrachloride and hydrogen fluoride at high temperature in an autoclave [refer to J. Org. Chem., 44, 2907 (1979)], Method (3) of: reacting phenolic compounds with $(CF_3)_2S(OCF_3)_2$ [refer to Inorg. Chem., 17, 2173 (1978)], Method (4) of: leading to phenyl thiochloroformate ($C_6H_5OCSCl$) by reacting phenols with thiophosgene, and treating with molybdenum hexafluoride ($MoF_6$) [refer to Fr. Demande 2,214,674 (1974) and Chem. Abstr., 82, 155,757 (1975)], and Method (5) of: leading to phenyl xanthate($C_6H_5OCSSCH_3$) by the reaction of phenols with carbon disulfide and methyl iodide followed by reacting this phenyl xanthate with a hydrogen fluoride-pyridine mixture and 1, 3-dibromo-5, 5-dimethylhydantoin [refer to Tetrahedron Lett., 33, 4173 (1992)].

Further, as for synthetic methods for (trifluoromethyl) trifluoromethane sulfonate as a (trifluoromethyl) sulfonate compound derived from sulfonic acid, the followings are known:

Method (6) of: decomposing the peroxide ($CF_3SO_2OOSO_2CF_3$) obtained by electrolysis of trifluoromethanesulfonic acid at low temperature [refer to Inorg. Chem., 4, 1010(1965)], Method (7) of: heating a mixture of trifluoromethanesulfonic acid and fluorosulfonic acid [refer to Synthesis, 319 (1976) and Inorg. Nucl. Chem. Letters, 16, 195 (1980)], Method (8) of: reacting silver trifluoromethanesulfonate obtained by reacting trifluoromethanesulfonic acid with silver oxide or silver nitrate, with trifluoromethyl iodide at high temperature in an autoclave [refer to Tetrahedron Lett., 40, 3865 (1979)], and Method (9) of: heating S-(trifluoromethyl) dibenzothiophenium trifluoromethanesulfonate obtained by reacting trifluoromethanesulfonic acid with 2-(trifluoromethylthio)biphenyl and fluorine gas, or its 3, 7-dinitro derivatives [refer to J. Am. Chem. Soc., 115, 2156 (1993)].

Further, the following synthetic method for alkyl (trifluoromethyl)ethers by trifluoromethylation of alkylalcohols is known:

Method (10) of: obtaining methyl or ethyl(trifluoromethyl) ethers by decomposition of trifluoromethanediazohydroxide at −50 to −55° C. which was produced by reaction of hydroxylamine with trifluoronitrosomethane at −75° C. in methanol or ethanol [refer to J. General Chem. USSR, 38, 685 (1968)].

In addition, the following synthetic method for alkyl (trifluoromethyl)ethers is known:

Method (11) of: reacting alkyltrifluoromethanesulfonates or activated alkylbromide with tris(dimethylamino)sulfonium trifluoromethoxide [for this compound, refer to J. Am. Chem. Soc., 107, 4565 (1985)] [for this method, refer to J. Carbohydrate Chem., 4, 545 (1985) and The Proceeding of the 67th Spring Annual Meeting of the Chemical Society of Japan, II, 3 C2 34, 767 (1994)].

However, the said methods have serious defects as follows:

Methods (1), (4) and (5) need multi-step reaction processes and must use highly toxic chlorine gas, hydrogen fluoride, thiophosgene, molybdenum hexafluoride, carbon disulfide and the like;

Method (2) results in a low yield (10%) of (trifluoromethyl) phenyl ether itself; besides it needs high pressure and high temperature using highly toxic hydrogen fluoride as the reaction condition;

In method (3), the synthesis of $(CF_3)_2S(OCF_3)_2$ used is extremely complex and must handle highly toxic substances (fluorine gas, chlorine gas, fluorophosgene and the like) in the synthesis;

In method (6), in addition to sulfonic acids used being limited, the highly dangerous explosive peroxides must be decomposed under careful control, and further electrolysis at a low temperature where the reaction condition is limited must be used;

In method (7), in addition to sulfonic acids used being limited, the yield of the objective is very low, the isolation is difficult because of generating many byproducts, and it needs a long reaction time at high temperature under conditions of super strong acidity;

Method (8) must use costly silver salts,

Method (9) must use a highly toxic fluorine gas and sulfonic acids are limited to super strong acids. Thus, these conventional methods cannot be widely used as useful synthetic methods for trifluoromethyl compounds.

Further, method (10) has problems related to the handling of the highly toxic gas, trifluoronitrosomethane and the controlling of the reaction due to the necessary decomposition reaction of trifluoromethanediazohydroxide, an unstable intermediate. Furthermore, as this is a reaction with solvent molecules, the range of application is extremely narrow and is not a widely-used method for trifluoromethylation.

Method (11) has problems in the isolation and purification of the objective (trifluoromethyl)ether compounds because many monofluorinated byproducts are generated. In addition, tris(dimethylamino)sulfonium trifluoromethoxide used in this reaction must be synthesized using highly toxic fluorophosgene as the starting material. Accordingly, method (11) is not a useful preparation method for trifluoromethyl compounds.

On the other hand, S-(trifluoromethyl) dibenzothiophenium salts and their analogous compounds are accepted as a useful trifluoromethylating agent [refer to J. Am. Chem. Soc., 115, 2156 (1993) and JP Patent Opening 3-197479]. However, when this agent is used for the trifluoromethylation of phenolic compounds, one drawback is that the yield is extremely low.

Further, (perfluoroalkyl)phenyliodonium trifluoromethanesulfonate (FITS reagent) and their analogs are known as perfluoroalkylating agents that have more than two carbons. However, reacting these with phenols usually fails to give (perfluoroalkyl) phenyl ethers, while a mixture of ortho- and para- (petfluoroalkyl)phenols is obtained by nuclear substitution [refer to Chem. Lett., 1663 (1981)]. Consequently, it has the serious defect that the method cannot be used as a preparation method for (perfluoroalkyl) phenyl ethers.

Considering these previous situations, the present inventors in the previous application have found 2'-(perfluoroalkoxy)biphenyl-2-diazonium salt or its derivatives as a perfluorinating agent which can readily perfluorinate an oxygen atom, nitrogen atom and the like in one step under mild conditions (refer to JP Patent Opening 7-330703: hereinafter, sometimes refer red to as the previous invention).

However, it was found that the yield and the range of application (namely, possible substances for perfluoroalkylation) of the perfluoroalkylation reaction when using 2'-(perfluoroalkoxy)biphenyl-2-diazonium salt and its derivatives as perfluoroalkylating agents for the perfluorination of an oxygen atom, nitrogen atom and the like, still need to be improved.

Further, 4-t-butyl-2'-(perfluoroalkoxy)biphenyl-2-diazonium salt, which is one typical example of the derivatives in the previous invention and the closest compound to the present invention has the problem of storability as a perfluoroalkylating agent, because it has comparatively low stability and gradually decomposes at room temperature. And the yield of the perfluoroalkylation reaction needs to be improved (refer to Examples 25, 26 and 38 of JP Patent Opening 7-330703 and Comparative Example 3 of the present invention as described later).

Further, 2'-(perfluoroalkoxy)biphenyl-2-diazonium salt [following general formula (A)], as shown in the following reaction scheme (a), eliminates nitrogen under the condition of a perfluoroalkylation reaction and is converted to an unstable active species (intermediate), O-(perfluoroalkyl) dibenzofuranium salt [following general formula (B)] which is expected to act as aperfluoroalkylating agent [refer to Chemical Reviews, 96, 1757–1777 (1996)]. The yield of the perfluoroalkylating reaction was insufficient, however.

Reaction Scheme (a)

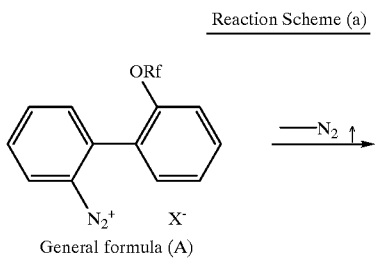

General formula (A)

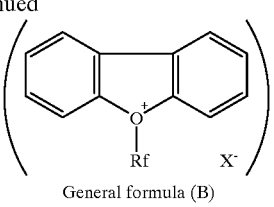

General formula (B)

OBJECTS OF THE INVENTION

The present invention has been conducted considering the above situations, and the objects are to provide O-(perfluoroalkyl)dibenzofuranium salt derivatives as comparatively stable perfluoroalkylating agents (such that the yield of the perfluoroalkylation reaction is high, the range of application is wide, and the self-decomposition is controlled), intermediates for their preparation, a preparation method for their intermediates, perfluoroalkylating agents and a perfluoroalkylation method.

COSTITUTION OF THE INVENTION

Considering such situations and after exhaustive studies, the present inventors have found that the low yield of the perfluoroalkylation reaction and the narrow range of application are caused by self-decomposition of the compound represented by general formula (B) of the above active species prior to the perfluoroalkylation reaction under the conditions of the perfluoroalkylation reaction.

The present inventors have completed the present invention based on the following findings: that O-(perfluoroalkyl)dibenzofuranium salt derivatives having a tert-butyl group at a specific position are self-decomposition-repressed and comparatively stable derivatives;

consequently, the perfluoroalkylation proceeds at a good yield; further, the range of application can be expanded widely; and 5-t-butyl-2'-(perfluoroalkoxy)biphenyl-2-diazonium salts which are precursors (preparation intermediates) of the said O-(perfluoroalkyl)dibenzofuranium salt derivatives are storable at room temperature and make a good handling compound having sufficient stability (refer to the below-described Example and Comparative Example, especially Example 15 and Comparative Example 3).

Namely, the present invention relates to the O-(perfluoroalkyl)dibenzofuranium salt derivatives (hereinafter, referred to as the derivatives of the present invention) represented by the following general formula (1).

General formula (1)

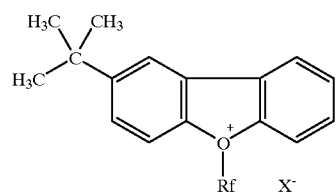

(wherein Rf in the above general formula (1) is a C1–10 perfluoroalkyl group and X$^-$ is a conjugate base of the Brönsted acid).

Further, the present invention provides intermediates for the preparation of O-(perfluoroalkyl)dibenzofuranium salt derivatives that comprise biphenyldiazonium salt derivatives represented by the following general formula (2) (hereinafter, referred to as the first intermediates of the present invention), which are useful as the intermediates for preparation of the present inventive derivatives as well as perfluoroalkylating agents.

General formula (2)

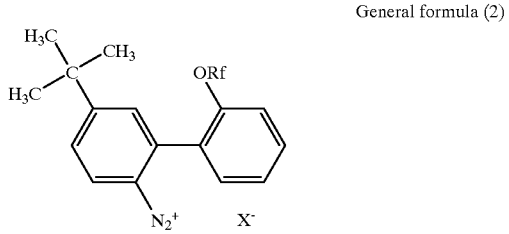

(wherein Rf in the above general formula (2) is a C1–10 perfluoroalkyl group and X⁻ is a conjugate base of the Brönsted acid).

Further, the present invention provides intermediates for the preparation of O-(perfluoroalkyl)dibenzofuranium salt derivatives that comprise aminobiphenyl derivatives represented by the following general formula (3) (hereinafter, referred to as the second intermediates of the present invention), which are useful as intermediates for the preparation of the first intermediates of the present invention.

General formula (3)

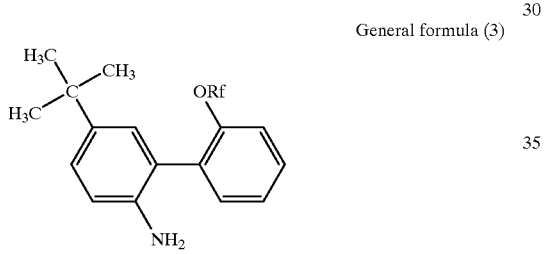

(wherein Rf in the above general formula (3) is a C1–10 perfluoroalkyl group).

Further, the present invention also provides perfluoroalkylating agents (hereinafter, referred to as the perfluoroalkylating agents of the present invention) which comprise at least either the said O-(perfluoroalkyl)dibenzofuranium salt derivatives represented by the said general formula (1), or the biphenyldiazonium salt derivatives represented by the said general formula (2) as intermediates for the preparation of the O-(perfluoroalkyl)dibenzofuranium salt derivatives, as compounds useful as perfluoroalkylating agents.

First, in the present inventive derivatives and the present inventive intermediates (hereinafter, sometimes referred to as the present inventive compounds), represented by the said general formulas (1)–(3), Rf is a C1–10 perfluoroalkyl group, and for example, is illustrated as $CF_3$, $C_2F_5$, $C_3F_7$, $C_4F_9$, $C_5F_{11}$, $C_6F_{13}$, $C_7F_{15}$, $C_8F_{17}$, $C_9F_{19}$, $C_{10}F_{21}$ and the like.

Further, in the present inventive compounds as shown in the said general formulas (1) and (2), X⁻ is a conjugate base of the Brönsted acid and the conjugate base of a strong Brönsted acid for which the acid dissociation exponent pKa is not more than 1 is preferable; for example, illustrated as $SbF_6^-$, $BF_4^-$, $PF_6^-$, $AsF_6^-$, $HSO_4^-$, $^-OSO_2CF_3$, $^-OSO_2C_4F_9$, $^-OSO_2F$, $^-OSO_2Cl$ and the like. Among them, because the perfluoroalkylation reaction shows high yields, $SbF_6^-$, $PF_6^-$ and $AsF_6^-$ are more preferable and $SbF_6^-$ is especially preferable.

The present inventive O-(perfluoroalkyl)dibenzofuranium salt derivatives represented by the general formula (1), the biphenyldiazonium salt derivatives represented by the general formula (2) and the aminobiphenyl derivatives represented by the general formula (3) can be prepared as shown in the following Reaction Scheme (1). The aminobiphenyl derivatives represented by general formula (3) can be also prepared by the method shown in the following Reaction Scheme (2). Furthermore, the method in this Reaction Scheme (2) has a cost advantage and is suitable for large-scale synthesis. Among the Reaction processes, reaction process (vi) is a meaningful preparation method found by the present inventors in the present invention.

Reaction Scheme (1)

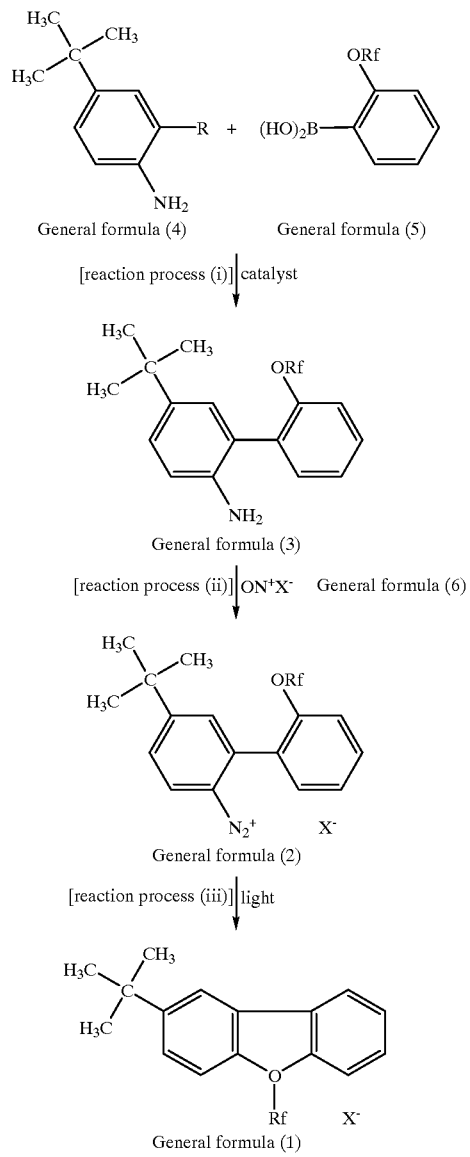

(wherein R in the said general formula (4) is a halogen atom, Rf in the said general formulas (5), (3), (2) and (1) is a C1–10 perfluoroalkyl group, and X⁻ in the said general formulas (6), (2) and (1) is a conjugate base of the Brönsted acid).

Next, the preparation methods of the present inventive compounds are illustrated in turn through the above reaction processes (i), (ii) and (iii).

[Reaction process (i)]:

The present process is to obtain the aminobiphenyl derivatives (the second intermediates of the present invention) represented by the said general formula (3) by reacting 2-halo-4-t-butylanilines represented by the said general formula (4) with 2-(perfluoroalkoxy)phenylboric acids represented by the said general formula (5) in the presence of a catalyst.

As for the 2-halo-4-t-butylanilines represented by the said general formula (4) used in the present process, 2-iodo-4-t-butylaniline, 2-bromo-4-t-butylaniline and 2-chloro-4-t-butylaniline are illustrated; among them, 2-bromo-4-t-butylaniline is preferable in terms of economy and good yield. 2-Halo-4-t-butylanilines represented by the said general formula (4) and 2-(perfluoroalkoxy)phenylboric acids represented by the said general formula (5) used in the present process are commercially available or can be readily synthesized.

Further, as for the said catalyst used in the present process, any known catalyst may be used, but $Pd(PPh_3)_4$ is especially preferable.

Further, the use of solvents in the present process is preferable and the following solvents are illustrated; for example: ethers such as diethyl ether, tetrahydrofuran, dimethoxyethane and dioxane; esters such as ethyl acetate; aprotic solvents such as dimethylformamide and dimethylsulfoxide; water and the like ; or a mixture of these solvents.

The reaction temperature is within the range 0–200° C., preferably in the range room temperature to 150° C. The usage amount of 2-halo-4-t-butylaniline represented by the said general formula (4) is not less than 0.4 mol to 1 mol of 2-(perfluoroalkoxy)phenylboric acid represented by the said general formula (5), preferably in the range 0.5–1.5 mol in terms of economy and yield. The usage amount of the catalyst may be the so-called catalytic amount. Herein, the reaction in the present process proceeds with a good reaction yield and efficiency in the presence of carbonate salts or bicarbonate salts such as sodium carbonate, sodium bicarbonate or potassium bicarbonate as a neutralizer.

[Reaction process (ii)]:

The present process is to obtain the biphenyldiazonium salt derivatives (the first intermediates of the present invention) represented by the said general formula (2) by the reaction of the aminobiphenyl derivatives represented by the said general formula (3) obtained in reaction process (i) with the nitroso compounds represented by the said general formula (6).

The nitroso compounds represented by the said general formula (6) are, for example, illustrated by $ON^+SbF_6^-$, $ON^+AsF_6^-$, $ON^+PF_6^-$, $ON^+BF_4^-$, $ON^+HSO_4^-$, $ON^{+-}OSO_2CF_3$, $ON^{+-}OSO_2C_4F_9$, $ON^{+-}OSO_2F$, $ON^{+-}OSO_2Cl$ and the like.

The usage amount of these nitroso compounds is preferably within the range 0.8–2 mol to 1 mol of the aminobiphenyl derivatives represented by the said general formula (3), but more preferably within the range 0.9–1.5 mol to give products with good yields.

The use of solvents in the present process is preferable; for example, halogenated hydrocarbons such as methylene chloride, chloroform, carbon tetrachloride and dichloroethane; halogenated aromatic compounds such as chlorobenzene, dichlorobenzene and benzotrifluoride; ethers such as diethyl ether, tetrahydrofuran, dioxane and dimethoxyethane; or a mixture of these solvents. The reaction temperature is preferably within the range –100° C. to +40° C., more preferably within the range –80° C. to room temperature in terms of yield and efficiency.

[Reaction process (iii)]:

The present process is to obtain the O-(perfluoroalkyl)dibenzofuranium salt derivatives (the present inventive derivatives) represented by the said general formula (1) by photo-irradiation of the biphenyldiazonium salt derivatives represented by the said general formula (2) obtained in reaction process (ii). The light source for photo-irradiation can be any light source used in general photochemical reactions which radiate light including wavelengths of at least 180–400 nm, such as a low pressure mercury lamp, high pressure mercury lamp and incandescent lamp.

This photo-irradiation may be usually conducted at reaction temperature within the range –200° C. to –30° C., preferably in the range –200° C. to –60° C. to give a good yield of O-(perfluoroalkyl)dibenzofuranium salt derivatives of the present invention by repressing self-decomposition of the product.

Although the present process does not always need solvents, use of the solvents is preferable in order to increase the efficiency of the photo-irradiation, and halogenated hydrocarbons such as methylenechloride, chloroform, carbon tetrachloride and dichloroethane are preferably illustrated.

As the O-(perfluoroalkyl)dibenzofuranium salt derivatives of the present invention cause self-decomposition at not less than –30° C. as shown later in Example 3, isolation can be performed by aftertreating at not more than –30° C., preferably not more than –60° C.

According to the perfluoroalkylating agents of the present invention, there can be used at least either the said O-(perfluoroalkyl)dibenzofuranium salt derivatives (the present inventive derivatives) represented by the said general formula (1) or the biphenyldiazonium salt derivatives (the first intermediates of the present invention) represented by the said general formula (2) as a perfluoroalkylating agent.

According to the present invention, nucleophiles (which especially have an oxygen atom or nitrogen atom capable of coupling with the perfluoroalkyl group) can be perfluoroalkylated by reacting perfluoroalkylating agents which comprise at least either the said O-(perfluoroalkyl)dibenzofuranium salt derivatives, or the said biphenyldiazonium salt derivatives (the first intermediates) which are intermediates in the preparation of the said O-(perfluoroalkyl)dibenzofuranium salt derivatives with the said nucleophiles.

Namely, when using the present inventive derivatives isolated as perfluoroalkylating agents, the perfluoroalkylation reaction can be conducted with good yields, while this reaction can be also performed using the first intermediate of the present invention which is sometimes more practical.

In the latter case, after transforming the said biphenyldiazonium salt derivatives to the said O-(perfluoroalkyl)dibenzofuranium salt derivatives by light or heating, these can be reacted with the said nucleophiles.

Namely, when the perfluoroalkylating reaction is conducted using the first intermediate of the present invention, the O-(perfluoroalkyl)dibenzofuranium salt derivatives of the present invention initially generated by photoreaction may be reacted with the nucleophiles without isolation, or the first intermediate of the present invention may be mixed with the nucleophiles from the start, then submitted to the said photoreaction or thermal reaction heating at greater than room temperature (refer to Example 15).

As for the solvents used in the perfluoroalkylation reaction, the solvents used in the said photoreaction are preferable as illustrated; if the nucleophile is liquid, it can also serve as a reaction solvent.

Reaction Scheme (2)

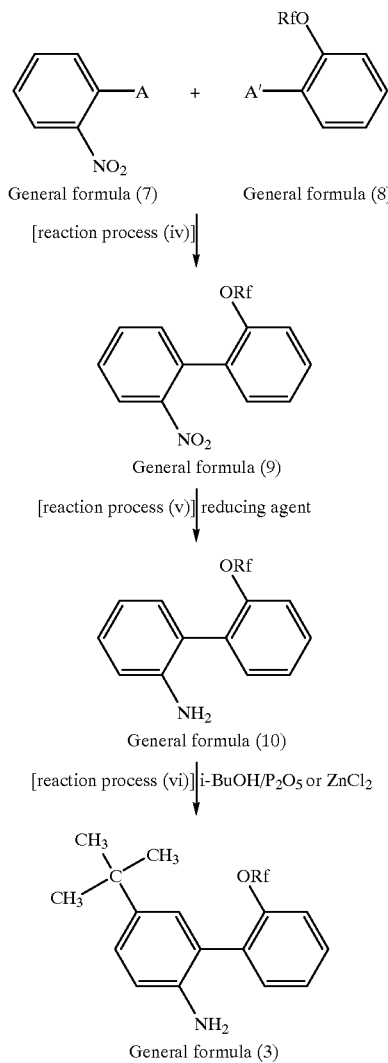

(wherein Rf in the said general formula is the same as described above; A and A' may be a bromine atom or an iodine atom, and may be either the same or different).

The compounds represented by general formula (7) or (8) which are used in Reaction Scheme (2) are known themselves and are commercially available.

The compounds in general formula (7) are exemplified as follows:

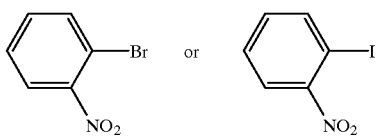

and the following are examples of the compounds in general formula (8):

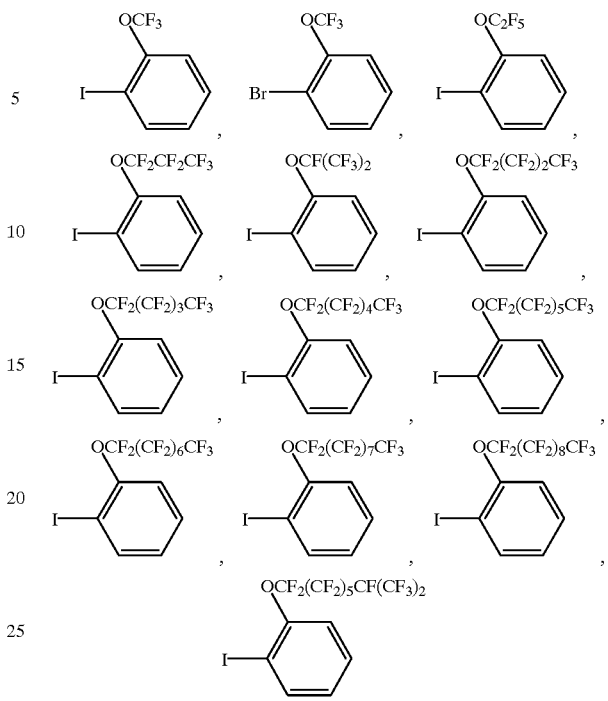

Next, the above reaction processes (iv), (v) and (vi) are illustrated.

[Reaction process (iv)]:

Reaction process (iv) prepares the nitrobiphenyl compounds in the said general formula (9) by reacting the nitro compounds in the said general formula (7) with the perfluoroalkoxy compounds in the said general formula (8) in the presence of copper.

The reaction in process (iv) can proceed with out any solvents, while the reaction can be also carried out in ordinary solvents; for example, aromatic compounds such as benzene, toluene, xylene, isopropylbenzene, isopropyltoluene and nitrobenzene, or polar solvents such as sulfolane, dimethylsulfolane, dimethylformamide, pyridine and lutidine.

The reaction temperature can usually be selected from the range 100° C. to 250° C., preferably 150° C. to 220° C. to result in a good yield.

For the ratio of the usage amount of the perfluoroalkoxy compounds in the said general formula (8) to the nitro compounds in the said general formula (7), the normal use of 0.5–2 mol, especially 0.8–1.5 mol, to 1 mol of the latter is appropriate.

Further, for the copper, the use of copper powder is normally preferable, with the usage amount within the range 1–10 g atom; 2–7 g atom to 1 mol of the nitro compounds in the said general formula (7) is appropriate.

[Reaction process (v)]:

The reaction process (v) prepares the aminobiphenyl compounds represented by the said general formula (10) by reducing the nitrobiphenyl compounds represented by the said general formula (9) obtained from reaction process (iv) using a reducing agent.

The reducing agent used in process (v) can use Sn/HCl and the like, which are usually used as a reducing agent for the nitro group. The use of solvents in this reaction to result in a good yield is preferable; for example, alcoholic solvents such as methanol and ethanol are preferable. The usage amount of the reducing agent is selected suitably corresponding to the amount of materials, nitrobiphenyl compounds consumed. The reaction temperature can normally be selected in the range from room temperature to 150° C., preferably 50° C.–100° C. to result in a good yield.

[Reaction process (vi)]:

Reaction process (vi) prepares the aminobiphenyl derivatives represented by the said general formula (3) by reacting the aminobiphenyl compounds represented by the said general formula (10) with isobutyl alcohol in the presence of phosphorous pentaoxide ($P_2O_5$) or zinc chloride ($ZnCl_2$). In this process (vi), isobutyl alcohol is preferably used as a reaction solvent. If other solvents are used, polar solvents except isobutyl alcohol are used. Inert solvents with a high boiling point can include sulfolane (b.p. 285° C.), nitrobenzene (b.p. 210.9° C.) and o-dichlorobenzene (b.p. 179.2° C.). The reaction temperature is generally 100–3000° C., and preferably 150–260° C. Further, the reaction molar ratio is usually aminobiphenyl/$P_2O_5$=1/1–1/10, and preferably 1/1–1/3. In addition, at least 1-equivalent of isobutyl alcohol, and if used also as a solvent, preferably 1–50 equivalents are preferably used.

The method used for isolation of the compounds in general formula (3) is distillation under a reduced pressure, column chromatography and the like.

INDUSTRIAL APPLICATION

According to the derivatives of the present invention, as shown in the O-(perfluoroalkyl)dibenzofuranium salt derivatives represented by the following general formula (1), by substituting a tertiary butyl group at the specific position; namely, the 2-position on the dibenzofuranium ring, self-decomposition of the derivatives is repressed. As a result, the perfluoroalkylation reaction gives a good yield and can widely enlarge the range of application.

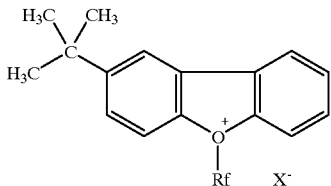

General formula (1)

(wherein Rf and $X^-$ in the said general formula (1) are the same as described above).

Further, according to the first intermediates of the present invention composed of the biphenyldiazonium salt derivatives represented by the following general formula (2), these are useful as the intermediates for preparation of the present inventive derivatives, as well as repressing the self-decomposition of these intermediates to preserve them at room temperature, becoming good handling compounds with enough stability to carry out the perfluoroalkylation reaction with a good yield, by substituting a tertiary butyl group at the specific position, namely, the 5-position on the biphenyl ring.

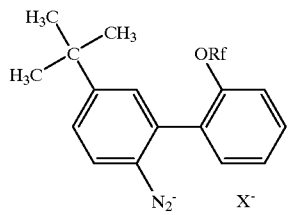

General formula (2)

(wherein Rf and $X^-$ in the said general formula (2) are the same as described above).

Further, the second intermediates of the present invention composed of the aminobiphenyl derivatives represented by the following general formula (3) are useful intermediates for the preparation of the first intermediates of the present invention and further the present inventive derivatives.

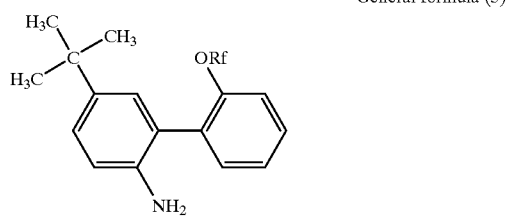

General formula (3)

(wherein Rf in the said general formula (3) is the same as described above).

Furthermore, according to the perfluoroalkylating agents of the present invention, the perfluoroalkylating agents comprise at least either O-(perfluoroalkyl) dibenzofuranium salt derivatives represented by the said general formula (1) or the preparation intermediates represented by the said general formula (2) of the O-(perfluoroalkyl) dibenzofuranium salt derivatives. As each compound has a tertiary butyl group at the specific position, namely, the 2-position on the dibenzofuranium ring or the 5-position on the biphenyl ring, when conducting the perfluoroalkylating reaction, the reaction is carried out with good yield by repressing the self-decomposition of the said derivatives and the said preparation intermediates, and further the range of application of the possible perfluoroalkylating substances can be widely enlarged.

EXAMPLE

Next, the present invention will be specifically illustrated by the following Examples and Comparative Examples.

Example 1

[Reaction Process (i)]

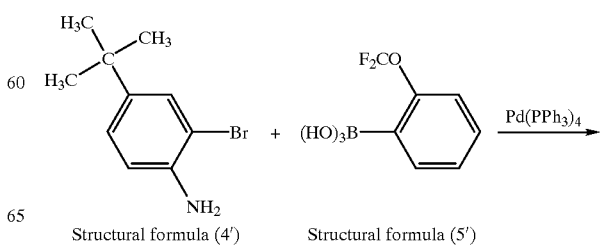

Structural formula (4')    Structural formula (5')

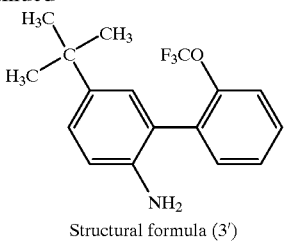

Structural formula (3')

A mixture of 7.0 g (0.031 mol) of 2-bromo-4-t-butylaniline represented by the above structural formula (4'), 12.7 g (0.061 mol) of 2-(trifluoromethoxy)phenylboric acid represented by the above structural formula (5'), 5.16 g (0.061 mol) of sodium bicarbonate, 3.55 g (0.003 mol) of tetra(triphenylphosphine)palladium and 330 mL of dimethoxyethane/water (volume ratio 10/1) was substituted with argon, and then refluxed for 64 hr.

After reaction, the mixture obtained was cooled and poured into an aqueous sodium bicarbonate solution. The solution was extracted with ether, the ether layer was washed with satd. brine and then dried with magnesium sulfate. After filtration of the extract obtained, the filtrate was concentrated and the residual was submitted to silica gel column chromatography (eluent: hexane/ethyl acetate=20/1–7/1) to obtain 8.3 g (87% yield) of 2-amino-5-t-butyl-2'-(trifluoromethoxy)biphenyl represented by the above structural formula (3') as an oil. The spectral data are as follows:

$^{19}$F-NMR (in CDCl$_3$, CFCl$_3$: internal standard); 57.6 ppm (3F, s, CF$_3$), $^1$H-NMR (in CDCl$_3$); δ7.45 (1H, dd, J=7.1, 1.8 Hz), 7.40–7.34 (3H, m), 7.22 (1H, dd, J=8.4, 2.3 Hz), 7.10 (1H, d, J=2.3 Hz), 6.77 (H, d, J=8.4 Hz) and 1.29 (9H, s, 3×CH$_3$), IR (neat): 2964, 1621, 1508, 1257, 1220 and 1168 cm$^-$, Mass Spectrum (m/e): 309 (M$^+$), 294 (M$^+$-CH$_3$) and 279 (M$^+$-2CH$_3$).

Example 2
[The Reaction Process (vi)]

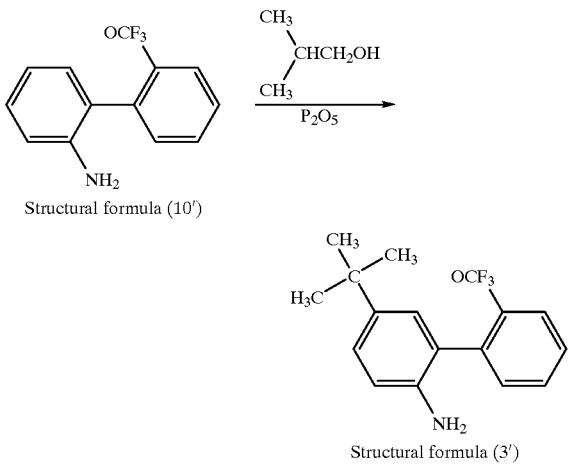

Structural formula (3')

A mixture of 253 mg (1.0 mmol) of 2-amino-21-(trifluoromethoxy)biphenyl represented by the above structural formula (10'), 156 mg (1.1 mmol) of phosphorous pentaoxide and 185 μL (2.0 mmol) of isobutyl alcohol was sealed in a tube and reacted at 220° C. for 12 hr. After cooling to room temperature, extracted with aqueous NaOH and ether, washing with water and satd. brine, the solution was dried with MgSO$_4$ and concentrated. Generation of 71% yield of the objective represented by the above structural formula (3') was confirmed by measurement of $^{19}$F-NMR of the concentrated oily product.

Example 3
[Reaction Process (ii)]

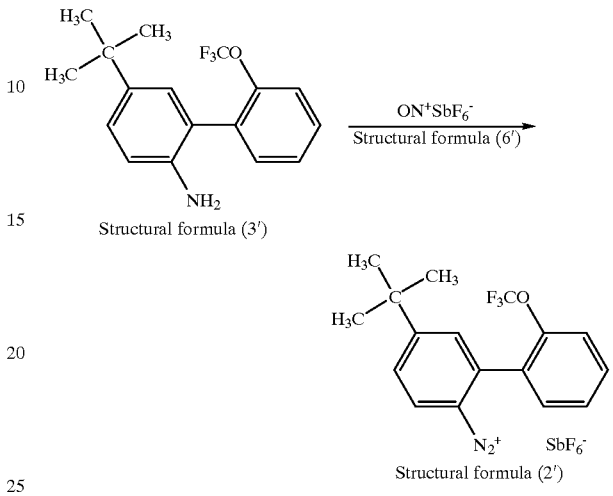

A solution of 7.17 g (0.023 mol) of 2-amino-5-t-butyl-2,-(trifluoromethoxy)biphenyl represented by the above structural formula (3') in 46 mL of diethyl ether was cooled to −78° C. in a dry ice-acetone bath, and 6.47 g (0.024 mol) of nitrosonium hexafluoroantimonate represented by the above structural formula (6') was added to this mixture while stirring. The reaction was completed by raising the bath temperature to 10° C. over 3 hr. Here, an additional 10 mL of diethyl ether was added at 5° C.

After reaction, the deposited crystals were filtered. The crystals were washed well with diethyl ether, and dried under reduced pressure to obtain 7.43 g (58% yield) of 5-t-butyl-2'-(trifluoromethoxy)biphenyl-2-diazonium hexafluoroantimonate [structural formula (2')].

The physical properties and the spectrum data are as follows:

M. p. (with decomposition); 84.7–85.8° C., $^1$H-NMR (in CDCl$_3$); δ8.67 (1H, d, J=8.9 Hz), 7.96 (1H, dd, J=8.9, 1.9 Hz), 7.77 (1H, d, J=1.9 Hz), 7.74–7.69 (2H, m), 7.63 (1H, dt, J=1.0, 7.7 Hz), 7.54 (1H, d, J=8.3 Hz) and 1.44 (9H, s, t-C$_4$H$_9$), $^{19}$F-NMR (in CDCl$_3$, CFCl$_3$: internal standard); 58.4 ppm (3F, S, CF$_3$), IR (KBr); 2974, 2262 (N≡N$^+$), 1589, 1560, 1248, 1220, 1196 and 1071 cm$^1$, Mass Spectrum (FAB method): 321 [(M-SbF$_6$)$^+$], High Resolution Mass Spectrum: Calcd C$_{17}$H$_{16}$F$_3$N$_2$O [(M-SbF$_6$)$^+$] 321.12147, Found 321.12033.

Generally, diazonium salts carry the risk of decomposition (explosion); However, as described above, because the decomposition temperature of 5-t-butyl-2'-(trifluoromethoxy)biphenyl-2-diazonium hexafluoroantimonate [m.p. (with decomposition) 84.7–85.8° C.], which is one of the first intermediates of the present invention represented by the said structural formula (2'), is about 27° C. higher than the decomposition temperature of the known isomeric form, 4-t-butyl-2'-(trifluoromethoxy)biphenyl-2-diazonium hexafluoroantimonate [m.p. (with decomposition) 58–60° C., Example 26 of JP Patent Opening 7–330703], it can be handled at room temperature without any trouble. In addition, safety for storage and transport is remarkably high.

Example 4

[Reaction Process (iii)]

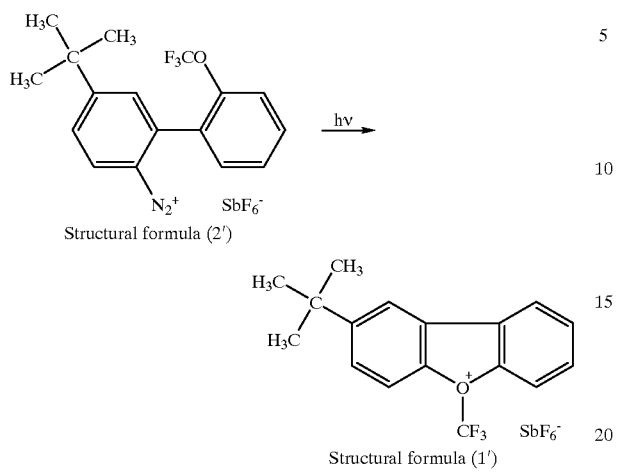

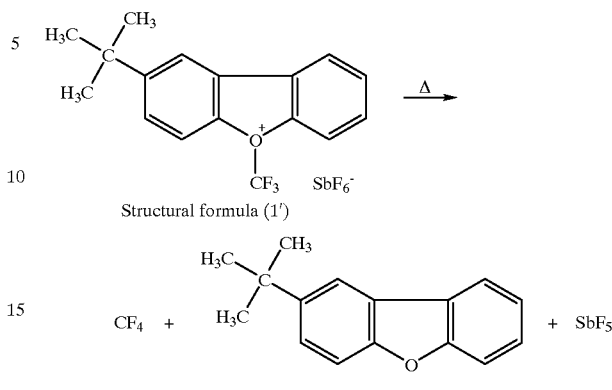

6.5 mg of 5-t-butyl-2'-(trifluoromethoxy)biphenyl-2-diazonium hexafluoroantimonate represented by the said structural formula (2'), 0.6mL of deuteromethylenechloride, and 1.1 mg of benzotrifluoride as an internal standard for $^{19}$F-NMR were charged into a Pyrex glass tube for NMR, and sealed after nitrogen substitution.

The NMR tube was placed in a bath (Pyrex glass container) cooled to −106° C., and was irradiated for 45 min from about 2 cm away with a high pressure mercury lamp (400W: main light energy wavelength: 253.7 nm) positioned outside of the bath. After irradiation, the $^{19}$F-NMR was measured at −80° C. The reaction solution inside the NMR tube at the low temperature of −106° C. is kept as a homogeneous solution both before and after irradiation.

On analyzing the NMR spectrum, 2-t-butyl-O-(trifluoromethyl)dibenzofuranium hexafluoroantimonate represented by the said structural formula (1') was produced with an 87% yield.

5-t-butyl-2-fluoro-2'-(trifluoromethoxy)biphenyl (8%) and 5-t-butyl-2-chloro-2'-(trifluoromethoxy)biphenyl (3%) were generated as byproducts.

The analytical data for $^{19}$F-NMR are as follows:

$^{19}$F-NMR (in CD$_2$Cl$_2$, CFCl$_3$: internal standard); 52.7 ppm (s, CF$_3$), $^1$H-NMR (in CD$_2$Cl$_2$); δ8.30 (1H, dd, J=7.6, 1.5 Hz, 6-H), 8.21 (1H, d, J=2.3 Hz, 1-H), 8.09 (1H, dm, J=9.1 Hz, 9-H), 8.03 (1H, t, J=7.6 Hz, 7-H), 7.99 (1H, dq, J=9.5, 2.3 Hz, 4-H), 7.92 (1H, ddd, J=9.1, 7.6, 1.5 Hz, 8-H), 7.89 (1H, dd, J=9.5, 2.3 Hz, 3-H) and 1.44 (9H, s, 2-t-C$_4$H$_9$). Here, when raising the temperature of the above NMR tube up to −30° C. from −80° C., the signals corresponding to 2-t-butyl-O-(trifluoromethyl)dibenzofuranium hexafluoroantimonate disappeared almost completely, whereas a strong new signal 60.8 ppm corresponding to CF$_4$ appeared, and also signals corresponding to 2-t-butylbenzofuran were confirmed.

From these results, at temperatures higher not less than −30° C., as shown in the following Reaction Scheme (b), a self-decomposition of 2-t-butyl-O-(trifluoromethyl) dibenzofuranium hexafluoroantimonate [structural formula (1')] which is one of the present inventive derivatives proceeds prior to other ones.

Examples 5–14

(Photo-irradiation Followed by Various Perfluoroalkylation Reactions)

A solution of 5-t-butyl-2'-(trifluoromethoxy)biphenyl-2-diazonium hexafluoroantimonate (0.05 mmol) represented by the said structural formula (2') containing benzotrifluoride (0.025 mmol) as an internal standard for $^{19}$F-NMR in 0.4 mL of methylenechloride was charged into a Pyrex glass container, and this was irradiated for 70 min while being cooled in a bath (Pyrex glass container) at a temperature of −99° C. to −90° C., by a high pressure mercury lamp (400 W) positioned outside of the bath at about 2 cm distance from the container.

The resulting 2-t-butyl-O-(trifluoromethyl) dibenzofuranium hexafluoroantimonate which is one of the present inventive derivatives was generated in the reaction solution at −90° C. with a high yield (87–89%). Here, the reaction solution at a temperature of −99° C. to −90° C. was a homogeneous solution both before and after irradiation. After irradiation, the nucleophiles and the bases shown in the following Table 1 were added into the obtained reaction solution, keeping the temperature at −90° C., and reacted under the reaction conditions shown in the same Table 1. After reaction, the products were identified by comparing the $^{19}$F-NMR spectrum of the reaction solution with that of the known substance, and the yields of the products were calculated. The results are also shown in Table 1.

The yields of the products are the total yields from 5-t-butyl-2,-(trifluoromethoxy)biphenyl-2-diazonium hexafluoroantimonate [said structural formula (2')] 1 which is one of the first intermediates of the present invention, and the yields in parentheses in the Table are the yields from 2-t-butyl-O-(trifluoromethyl)dibenzofuranium hexafluoroantimonate [said structural formula (1')] which is one of the present inventive derivatives generated from photoreaction. Further, the yield of 2-t-butyl-O-(trifluoromethyl) dibenzofuranium hexafluoroantimonate, which is one of the present inventive derivatives, was calculated by deducting the total yield of 5-t-butyl-2-fluoro-2'-(trifluoromethoxy) biphenyl and 5-t-butyl-2-chloro-2'-(trifluoromethoxy) biphenyl (which are byproducts of the said photoreaction) obtained by the NMR analysis of the reaction mixture after perfluoroalkylation, from 100%.

TABLE 1A

| Example | Biphenyldiazonium salt derivative (using amount) | O-(Perfluoroalkyl) dibenzofuranium salt derivative (yield) | Nucleophile (using amount) | Base (using amount) | Reaction temperature (°C.) | Reaction time | Product Structural formula | Yield | ¹⁹F-NMR (ppm) (in CD₃CN, CFCl₃,: internal standard) |
|---|---|---|---|---|---|---|---|---|---|
| 5 | [biphenyldiazonium salt structure with OCF₃, C(CH₃)₂, N₂⁺ SbF₈⁻] (0.05 mmol) | [dibenzofuranium salt with O⁺–CF₃ SbF₈⁻, C(CH₃)₂] (87%) | CH₂CH₂OH (phenyl) (0.05 mmol) | 2-chloropyridine (0.05 mmol) | −90 → −10 | 3 h | Ph–CH₂CH₂OCF₃ | 70% (80%) | 59.8(s, CF₃) |
| 6 | [biphenyldiazonium salt structure] (0.05 mmol) | [dibenzofuranium salt] (88%) | 4-methylpyridine (0.05 mmol) | None | −90 → −10 | 3 h | 4-methyl-N-CF₃ pyridinium SbF₈⁻ | 56% (64%) | 60.5(s, CF₃) |
| 7 | [biphenyldiazonium salt structure] (0.05 mmol) | [dibenzofuranium salt] (87%) | pyridine (0.05 mmol) | None | −90 → −10 | 3 h | N-CF₃ pyridinium SbF₈⁻ | 61% (70%) | 60.5(s, CF₃) |

TABLE 1B

| Example | Biphenyldiazonium salt derivative (using amount) | O-(Perfluoroalkyl) dibenzofuranium salt derivative (yield) | Nucleophile (using amount) | Base (using amount) | Reaction temperature (°C.) | Reaction time | Product Structural formula | Yield | ¹⁹F-NMR (ppm) (in CD₃CN, CFCl₃; internal standard) |
|---|---|---|---|---|---|---|---|---|---|
| 8 | (0.05 mmol) | (88%) | PhNH₂ (0.05 mmol) | PhNH₂ (0.05 mmol) | −90 → −10 | 3 h | Ph–NHCF₃ | 81% (92%) | 55.1 (d, J=5.6Hz, CF₃) |
| 9 | (0.05 mmol) | (89%) | PhNHCH₃ (0.05 mmol) | PhNHCH₃ (0.05 mmol) | −90 → −10 | 3 h | Ph–N(CF₃)(CH₃) | 62% (70%) | 59.6 (s, CF₃) |
| 10 | (0.05 mmol) | (88%) | PhN(CH₃)₂ (0.05 mmol) | None | −90 → −10 | 6 h | Ph–N⁺(CF₃)(CH₃)₂ SbF₆⁻ | 43% (49%) | 73.5 (s, CF₃) |

TABLE 1C

| Example | Biphenyldiazonium salt derivative (using amount) | O-(Perfluoroalkyl) dibenzofuranium salt derivative (yield) | Nucleophile (using amount) | Base (using amount) | Reaction temperature (°C.) | Reaction time | Product Structural formula | Yield | ¹⁹F-NMR (ppm) (in CD₃CN, CFCl₃; internal standard) |
|---|---|---|---|---|---|---|---|---|---|
| 11 | [biphenyl with OCF₃ and C(CH₃)₂ and N₂⁺ SbF₆⁻] (0.05 mmol) | [dibenzofuranium CF₃ SbF₆⁻ with C(CH₃)₂] (87%) | PhCH₂NH₂ (0.05 mmol) | PhCH₂NH₂ (0.05 mmol) | −90 → −10 | 3 h | Ph-CH₂NHCF₃ | 64% (74%) | 57.2(d, J=7.4Hz, CF₃) |
| 12 | [biphenyl with OCF₃ and C(CH₃)₂ and N₂⁺ SbF₆⁻] (0.05 mmol) | [dibenzofuranium CF₃ SbF₆⁻ with C(CH₃)₂] (88%) | (C₂H₅)₂NH (0.05 mmol) | (C₂H₅)₂NH (0.05 mmol) | −90 → −10 | 3 h | (C₂H₅)₂NCF₃ | 43% (49%) | 59.3(s, CF₃) |
| 13 | [biphenyl with OCF₃ and C(CH₃)₂ and N₂⁺ SbF₆⁻] (0.05 mmol) | [dibenzofuranium CF₃ SbF₆⁻ with C(CH₃)₂] (88%) | PhOH (0.05 mmol) | [(CH₃)₂CH]₂NCH₂CH₃ (0.05 mmol) | −90 → −10 | 5.5 h | Ph-OCF₃ | 66% (75%) | 57.5(s) |

TABLE 1D

| Example | Biphenyldiazonium salt derivative (using amount) | O-(Perfluoroalkyl) dibenzofuranium salt derivative (yield) | Nucleophile (using amount) | Base (using amount) | Reaction temperature (°C.) | Reaction time | Product Structural formula | Yield | ¹⁹F-NMR (ppm) (in CD₃CN, CFCl₃; internal standard) |
|---|---|---|---|---|---|---|---|---|---|
| 14 | [biphenyldiazonium SbF₆⁻ with OCF₃ and C(CH₃)₂ groups] (0.05 mmol) | [dibenzofuranium SbF₆⁻ with CF₃ and C(CH₃)₂ groups] (88%) | [1-(2-naphthyl)ethanol] (0.05 mmol) | [1-(2-naphthyl)ethanol] (0.05 mmol) | −90 → −10 | 5.5 h | [1-(2-naphthyl)ethyl trifluoromethyl ether, CH₃-CH(OCF₃)-naphthyl] | 45% (51%) | 57.1(s) |

As shown in Examples 5–14, it was proved that the compounds of the present Examples have a wide range of application to an oxygen atom and nitrogen atom and become perfluoroalkylating agents with excellent yields. Examples 8–12 show examples of perfluoroalkylation to a nitrogen atom on arylamines and alkylamines.

Comparative Examples 1–2

Except for the use of 2'-(trifluoromethoxy)biphenyl-2-diazonium hexafluoroantimonate instead of 5-t-butyl-2'-(trifluoromethoxy)biphenyl-2-diazonium hexafluoroantimonate as the biphenyldiazonium salt derivative which is one of the first intermediates of the present invention, the others were conducted by perfluoroalkylation reaction as well as Example 5 or 6 after photoirradiation. The results are shown in the following Table 2.

Further, the yields of the products show the yields from the biphenyldiazonium salt derivatives, and the yields in parentheses show the yields from the O-(perfluoroalkyl) dibenzofuranium salt derivatives. In Comparative Examples 1 and 2, the reaction solutions at the temperature of −99° C. to −90° C. were heterogeneous solutions both before-and after photoirradiation.

Furthermore, the yields of the O-(trifluoromethyl) dibenzofuranium hexafluoroantimonate generated by photoirradiation in Comparative Examples 1–2 were calculated from the NMR analysis of the reaction mixture after the perfluoroalkylation reaction. As shown in the comparison of Examples 5 and 6 (with a t-butyl group on the 5-position of biphenyl group) with Comparative Examples 1 and 2 (without a t-butyl group), it was proved that the compounds having a specific substituent at a specific position such as the present Examples become excellent perfluoroalkylating agents for organic synthetic chemistry.

TABLE 2

| Comparative Example | O-(Perfluoroalkyl) | | Nucleophile (using amount) | Base (using amount) | Reaction temperature (° C.) | Reaction time | Product | | |
|---|---|---|---|---|---|---|---|---|---|
| | Biphenyldiazonium salt derivative (using amount) | dibenzofuranium salt derivative (yield) | | | | | Structural formula | Yield | $^{19}$F-NMR (ppm) (in CD$_3$CN, CFCl$_3$; internal standard) |
| 1 | (biphenyldiazonium SbF$_6^-$ salt, OCF$_3$, N$_2^+$) (0.05 mmol) | (dibenzofuranium SbF$_6^-$ salt with CF$_3$) (37%) | CH$_2$CH$_2$OH (phenyl) (0.05 mmol) | 2-chloropyridine (0.05 mmol) | −90 → −10 | 3 h | phenyl-CH$_2$CH$_2$OCF$_3$ | 11% (30%) | 59.8(s, CF$_3$) |
| 2 | (biphenyldiazonium SbF$_6^-$ salt, OCF$_3$, N$_2^+$) (0.05 mmol) | (dibenzofuranium SbF$_6^-$ salt with CF$_3$) (44%) | 4-methylpyridine (0.05 mmol) | None | −90 → −10 | 3 h | N-CF$_3$ pyridinium (4-CH$_3$) SbF$_6^-$ | 20% (45%) | 60.5(s, CF$_3$) |

Example 15 and Comparative Example 3

Under the reaction condition shown in the following Table 3, using 5-t-butyl-2'-(trifluoromethoxy)biphenyl-2-diazonium hexafluoroantimonate (Example 15) which is one of the first intermediates of the present invention, and 4-t-butyl-2'-(trifluoromethoxy)biphenyl-2-diazonium hexafluoroantimonate (Comparative Example 3) which is a known isomer of the said compound, respectively, a trifluoromethylation reaction of phenols by thermoreaction was performed. In any reaction, the reaction time shows the full consumption time taken for each biphenyldiazonium salt derivative. Accordingly, the yield does not change even if it takes a longer reaction time. The results are also shown in Table 3.

according to the later consideration. The electron donating effect of a t-butyl group, as shown in the Hammett substitution constant, is markedly changed by the positional difference of the substituent on the benzene ring. Namely, the electron donating effect of the t-butyl group ($\sigma_p^+ = -0.26$) at the para position is much higher than that ($\sigma_m = -0.09$) at the meta position. For this reason, the present inventive compounds represented by general formulas (1) and (2) having a t-butyl group at the para position receive a stronger stabilizing effect due to the butyl group to an oxonium group and a diazonium group which are strong electron attracting groups.

Namely, the O-(perfluoroalkyl)dibenzofuranium salt derivatives having a t-butyl group at the 2-position (para position) represented by general formula (1), which are the

TABLE 3

|  | Biphenyldiazonium salt derivative (using amount) | Nucleophile (using amount) | Reaction temperature (° C.) | Reaction time | Product Structural formula | Yield | $^{19}$F-NMR (ppm) (in CD$_3$CN, CFCl$_3$,: internal standard) |
|---|---|---|---|---|---|---|---|
| Example 15 | [5-t-butyl-2'-(trifluoromethoxy)biphenyl-2-diazonium SbF$_6^-$] (0.3 mmol) | [phenol-OH] (1.0 ml) | 43 | 24 h | [phenyl-OCF$_3$] | 60% | 57.5(s) |
| Comparative Example 3 | [4-t-butyl-2'-(trifluoromethoxy)biphenyl-2-diazonium SbF$_6^-$] (0.3 mmol) | [phenol-OH] (1.0 ml) | 43 | 3 h | [phenyl-OCF$_3$] | 37% | 57.5(s) |

As is shown by comparing Example 15 with Comparative Example 3, the yield of the product in Example 15 is extremely high, compared with that of Comparative Example 3 and it was proved that the compound of the present Example having a t-butyl group at a specific position becomes an excellent perfluoroalkylating agent.

Also the high yield of Example 15 compared to Comparative 3 is based on an efficient reaction with a coexisting nucleophile prior to self-decomposition because the stability of the O-(perfluoroalkyl)dibenzofuranium salt derivatives having a t-butyl group at the 2-position, which are the present inventive derivatives generated from the first intermediates of the present invention by thermoreaction, is higher than that of O-(perfluoroalkyl)dibenzofuranium salt derivatives having a t-butyl group at the 3-position as similarly generated for the Comparative Example 3. Further, because the thermoreaction time in Example 15 takes longer than Comparative Example 3, the objective trifluoromethylation reaction can proceed with good yield. This fact depends on the relatively higher stability of the present inventive derivatives and the first intermediates.

The remarkable difference of effect based on the specific position of this t-butyl group may be explained as follows present inventive derivatives, strongly stabilizes through the hyperconjugating resonance effect by the t-butyl group as shown in the following Scheme (a). Accordingly, because the present inventive derivatives represses the self-decomposition and are comparatively stable, a perfluoroalkylation reaction showing a high yield and wide range of application is obtained.

Scheme (a)

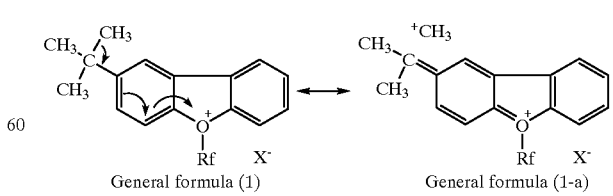

General formula (1)    General formula (1-a)

On the other hand, as shown in the following Scheme (b), the resonance structure [general formula (C-a)] of the 3-t-butyl-O-(perfluoroalkyl)dibenzofuranium salt derivatives represented by general formula (C) which are isomers [having a t-butyl group at the 3-position (meta position)] of the present inventive derivatives, is different from the structure of general formula (1-a) of the present invention. Accordingly, because a negative ion generated by hyperconjugation of the t-butyl group is isolated through one carbon atom, this ion can not directly interact with a positive ion on an oxygen atom and therefore the stabilizing effect is weak.

Accordingly, the 3-t-butyl-O-(perfluoroalkyl) dibenzofuranium salt derivatives represented by general formula (C), which are isomers of the present inventive derivatives, precede readily self-decomposition, and a satisfactory perfluoroalkylating reaction cannot be obtained.

Scheme (b)

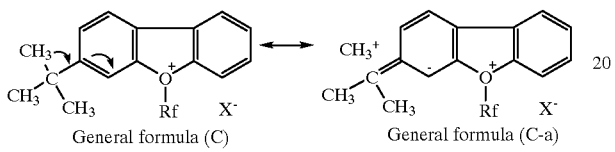

General formula (C)      General formula (C-a)

In addition, the biphenyldiazonium salt derivatives [general formula (2)] having a t-butyl group at the 5-position (para position) which are the first intermediates of the present invention, as shown in the following Scheme (c), exhibit a strong stabilizing effect based on the t-butyl group at the para position.

Therefore, the biphenyldiazonium salt derivatives [general formula (2)] which are the first intermediates of the present invention have a high stability and are highly stable at room temperature.

Scheme (c)

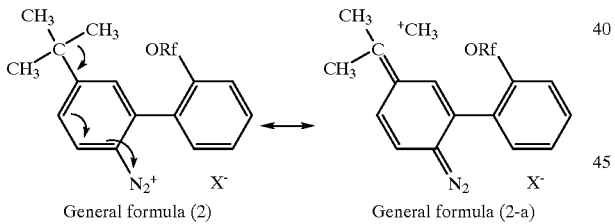

General formula (2)      General formula (2-a)

On the other hand, as shown in the following Scheme (d), the biphenyldiazonium salt derivatives having a t-butyl group at the 4-position (meta position) represented by the general formula (D), which are the isomers of the first intermediates (biphenyldiazonium salt derivatives) of the present invention, readily cause self-decomposition, because a cation species represented by the general formula (E), which is an active species generated from the self-decomposition liberating nitrogen (N$_2$), stabilizes through hyperconjugation at the meta position of the t-butyl group, as shown in the resonance structure represented by the general formula (E'). Therefore, the biphenyldiazonium salt derivatives represented by general formula (D) are unstabilized. Accordingly, the stability of the biphenyldiazonium salt derivatives represented by general formula (D) being the isomer is lower than the stability of the biphenyldiazonium salt derivatives which are the first intermediates of the present invention.

Scheme (d)

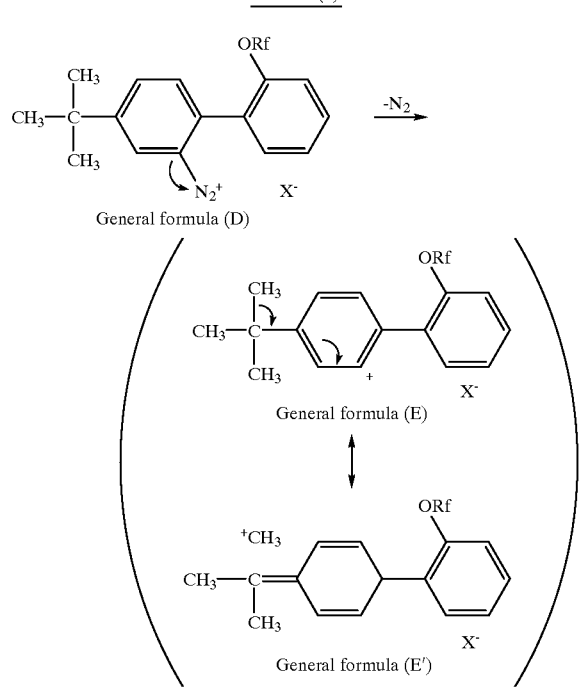

As described above, it is considered that the stability of the biphenyldiazonium salt derivatives and the O-(perfluoroalkyl)dibenzofuranium salt derivatives derived therefrom has been improved, and therefore their usefulness as perfluoroalkylating agents has been markedly improved by substituting the tertiary butyl group at a specific position, namely, the 5-position on the biphenyl ring (the 2-position on the dibenzofuranuim ring).

What is claimed is:
1. An O-(perfluoroalkyl)dibenzofuranium salt derivative represented by the following general formula (1),

General formula (1)

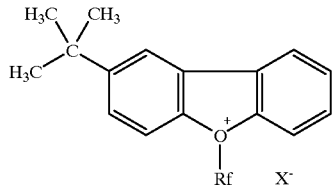

(wherein Rf in said general formula (1) is a C1–10 perfluoroalkyl group and X$^-$ is a conjugate base of a Brönsted acid).

2. The O-(perfluoroalkyl)dibenzofuranium salt derivative as claimed in claim 1 wherein said X$^-$ is SbF$_6^-$.

3. An intermediate for preparation of the O-(perfluoroalkyl)dibenzofuranium salt derivative having a biphenyldiazonium salt derivative represented by the following general formula (2),

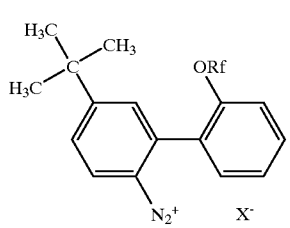

General formula (2)

wherein Rf in said general formula (2) is a C1–10 perfluoroalkyl group and X⁻ is a conjugate base of a Brönsted acid.

4. The intermediate for preparation of the O-(perfluoroalkyl)dibenzofuranium salt derivative as claimed in claim 3 wherein said X⁻ is $SbF_6^-$.

5. The intermediate for preparation of the O-(perfluoroalkyl)dibenzofuranium salt derivative having an aminobiphenyl derivative represented by the following general formula (3),

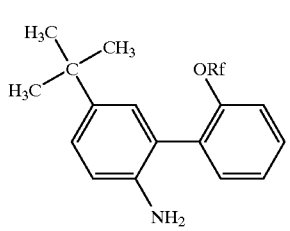

General formula (3)

(wherein Rf in said general formula (3) is a C1–10 perfluoroalkyl group).

6. A process of making compounds of formula (3) comprising the reaction of an aminobiphenyl defivative represented by the following general formula (10) with isobutyl alcohol in the presence of phosphorous pentoxide or zinc chloride,

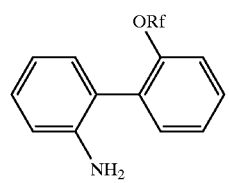

General formula (10)

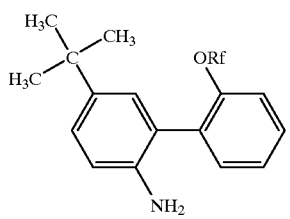

General formula (3)

wherein Rf in said general formulas (10) and (3) is a C1–10 perfluoroalkyl group.

7. A process of perfuoroalkylating a nucleophile comprinsing reacting an O-(perfluoroalkyl) dibenzofuranium salt derivative of claim 1 with a nucleophile.

8. The process as claimed in claim 7 wherein said O-(perfluoroalkyl) dibenzofuranium salt derivative is made from said biphenyldiazonium salt derivative by the action of light or heating in the presence of said nuclephile.

9. The process as claimed in claim 7 wherein said nucleophile has an oxygen atom or a nitrogen atom capable of coupling with a perfluoroalkyl group.

10. A process of perfluoroalkylating a nucleophile comprising the reaction of a biphenyldiazonium salt derivative, which is the intermediate for preparation of O-(perfluoroalkyl)dibenzofuranium salt derivative, with said nucleophile, said biphennyldiazonium salt derivative represented by the following general formula (2),

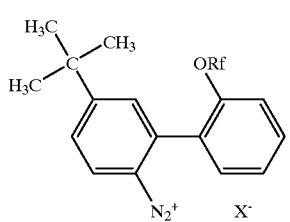

General formula (2)

wherein Rf in said general formula (2) is a C1–10 perfluoroalkyl group and X⁻ is a conjugate base of a Brönsted acid.

* * * * *